United States Patent
Hertel et al.

[11] Patent Number: 6,118,531
[45] Date of Patent: Sep. 12, 2000

[54] METHOD FOR IDENTIFYING PARTICLES IN A GASEOUS OR LIQUID CARRIER MEDIUM

[76] Inventors: Martin Hertel, Biberweg 12, D-07749 Jena; Torsten Wappler, Nollendorfer Strasse 25, D-07743 Jena, both of Germany

[21] Appl. No.: 09/358,270

[22] Filed: Jul. 21, 1999

Related U.S. Application Data

[63] Continuation-in-part of application No. 09/071,907, May 4, 1998, abandoned.

[30] Foreign Application Priority Data

May 3, 1997 [DE] Germany ............... 197 18 875

[51] Int. Cl.[7] ............................................. G01N 15/02
[52] U.S. Cl. ......................... 356/336; 356/340; 356/343
[58] Field of Search ........................ 356/335–343, 356/438, 435, 73; 250/574, 575, 222.2, 564

[56] References Cited

U.S. PATENT DOCUMENTS

| | | | |
|---|---|---|---|
| 3,822,095 | 7/1974 | Hirschfeld | 356/343 |
| 4,701,051 | 10/1987 | Buchhave et al. | 356/343 |
| 5,052,806 | 10/1991 | Snyder | 356/343 |
| 5,373,367 | 12/1994 | DeGunther et al. | 356/438 |
| 5,416,580 | 5/1995 | Trainer . | |
| 5,841,534 | 11/1998 | Lorenz | 356/342 |

FOREIGN PATENT DOCUMENTS

| | | |
|---|---|---|
| 0182618 | 5/1986 | European Pat. Off. . |
| 0493806A2 | 7/1992 | European Pat. Off. . |
| 4341573C1 | 3/1995 | Germany . |
| 4414166C1 | 12/1995 | Germany . |
| WO90/10215 | 9/1990 | WIPO . |

*Primary Examiner*—Hoa Q. Pham
*Attorney, Agent, or Firm*—Collard & Roe, PC

[57] ABSTRACT

The invention relates to a method for identifying the particles contained in a gaseous or liquid or carrier medium by measuring scattered light aimed at the medium. The method of the invention identifies particles of very small size and also measures the geometric shape of the particles. This is accomplished by simultaneously operating at least three light sources aimed at the volume to be analyzed, and detecting the scattered light with at least three detectors. The measured values of the detected light are correlated and evaluated to identify the particles.

11 Claims, 2 Drawing Sheets of U.S. patent application Ser. No. 09/071,907 filed on May 4, 1998 now abandoned.

BACKGROUND OF THE INVENTION

1. Field of the Invention

This invention relates to a method of identifying the particles contained in a gaseous or liquid carrier medium. In particular, this invention relates to a method of identifying these particles by measuring scattered light through the medium to be analyzed.

2. The Prior Art

Scattered light measurement for identifying and classifying the particles contained in aerosols or transparent liquid is known. In these measurements, a light beam is aimed at the medium to be analyzed. The beam is scattered when it impacts a particle in the carrier medium, and is measured by a detector. Based on this data, it is possible to determine various properties of the particle, for example, its size, size distribution, shape and position.

Optical particle measurement is applied particularly in fields where examination of small particles is not possible using conventional methods. These known methods and apparatuses are largely based on Mie scattering theory. This is described in DE 43 41 573 C1, and has significant drawbacks. First, the optical measuring arrangement of this method detects only the forward scattering component. Second, the proposed astigmatic focusing causes a loss of intensity, so that small particles cannot be detected at all. Finally, since only one detector is employed, the geometric shape of the detected particles cannot be determined.

The method and device defined by DE 44 14 165 C1 measures light scatter on particles by arranging a plurality of pulsated light sources one after the other in a section of a tube, along with a common receiver. However, this solution also has several drawbacks. Since only one detector is employed, the scattered light produced by the interaction of the light with the particle can be detected only under a fixed space angle. Successive pulsating of the various light sources does result in different angles of incidence on the volume being measured. However, angular resolution of the measured light relative to the position of the particle cannot be measured, because different cross sections of scatter are measured with predominantly nonspherical particles due to the different angles of irradiation. Consequently, the size and shape of the detected particles cannot be correctly determined.

An inspection of a plurality of planes of scatter is possible by a particle measuring apparatus shown in EP 0 493 806 A2. With this apparatus, a ring-shaped arrangement of the detectors is employed for measuring larger particles, and an arrangement of detectors mounted at greater angles is used for measuring smaller particles. However, inspecting several planes with the ring-shaped detector arrangement is only achieved with forward scatter. As with the previously discussed prior art documents, only one plane is available for measuring larger angles of light scatter. This apparatus consequently does not permit any exact determination of the shape of particles. Moreover, this solution is afflicted with the shortcomings associated with only one light source.

U.S. Pat. No. 5,416,580 to Trainer, the disclosure of which is herein incorporated by reference, discloses a method and a device for identifying the particles contained in a gaseous or liquid carrier medium by measuring scattered light. In this patent, at least three light sources are aimed sequentially at the volume to be measured, and at least three detectors are used. The detectors are operated simultaneously and the measured scattered light values acquired by the detectors are correlated and evaluated. The goal of this invention is to expand the range of angular movement within one plane of scatter by sequentially switching the light sources on and off, with the light sources being arranged in one plane.

However, like the arrangement shown in EP 0 493 806 A2, this does not permit any angle-resolved measurement in different planes of scatter. Even with a suitable arrangement of light sources and detectors for detecting a plurality of planes of scatter, operating the light sources sequentially has decisive drawbacks. For example, the light sources have to be switched on and off very rapidly in order to fully measure the same particle in the measured volume. In the case of nonspherical particles, operating the light sources sequentially has the risk that, in addition to measurement of different particles, rotation of the particle in the measured volume may lead to an angle of incidence of the subsequent light source that is no longer definable, and thus subject to incorrect interpretation.

In addition, it is not possible to exactly determine the shape of the particles using the structure shown in U.S. Pat. No. 5,416,580. Furthermore, with spherical particles flowing at a high rate, no suitable measurement is possible for identifying particle size and refractive index, because it is not certain that the same particle is always present in the measured volume during the course of the measurement.

U.S. Pat. No. 3,822,095 to Hirschfeld describes an apparatus that uses a single light source. The light is split up by a specially designed optic into three different virtual light sources. The Hirschfeld system consists of three optical units (a detector and an apparent light source) looking at different measurement volumes. They are measuring the flow at the same sample but not at the same spot within the medium. To determine the shape and material dependent properties, it is necessary to illuminate the particle by three physically different light sources at the same time and the same spot. This is because evaluating shape and material properties requires simultaneous measuring in different scattering planes with respect to the orientation of the particle. This can only be done by measuring within one common measuring volume at the same time. Hirschfeld measures different properties of the particles at different locations and different times with three different apparent light sources generated from one optical light source.

U.S. Pat. No. 4,701,051 to Buchhave et al. discloses a laser doppler apparatus (LDA) that uses only one light source to generate two virtual coherent light sources to provide an interference pattern in the measurement volume. Thus, only one physical light source is used together with several detectors. The LDA apparatus is therefore measuring in only one scattering plane with one light source. The aim is to determine velocity and size of the spherical particles. The LDA method is not applicable to non-spherical particles. A measurement of shape and material properties is thus not possible with LDA.

U.S. Pat. No. 5,052,806 to Snyder et al. describes a system with only one light source as well. Here, the beam is split and a frequency shift is applied. This measurement method is state of the art in optical physics and is called heterodyne measurement. It is necessary to have the frequency shift and the light from one light source because this measurement method is based on the coherence of the two virtual light sources generated by one laser (so only one physical light source is used.) Therefore, this method is not measuring the light coming from three different light sources, hitting the particle at the same time in the same measuring volume to provide a measurement of the scattered light in different scattering planes.

SUMMARY OF THE INVENTION

It is therefore an object of the present invention to provide a method for identifying the particles contained in a gaseous or liquid carrier medium using scattered light that overcomes the drawbacks of the prior art.

It is another object of the present invention to provide a method for identifying very small particle sizes, especially in the range of below 0.1 µm.

It is a further object of the invention to provide a method that determines the geometric shape of the detected particles.

These and other objects are accomplished by method for identifying particles in a gaseous or liquid carrier medium, comprising simultaneously operating at least three light sources aimed at the volume to be measured, and using at least three optical detectors. The particles are identified through correlated evaluation of the measured scattered light acquired by the detectors.

Each light source may be evaluated with respect to a single detector or multiple detectors. Alternatively, each detector may be evaluated with respect to a single light source, or multiple light sources. The light sources are preferably modulated with signals having different frequencies, phase relations and/or modulation depths. At least two light sources may be modulated with the same signals. Preferably, at least one light source is operated with a defined polarization of the light.

The detectors are evaluated selectively according to frequency with the use of modulated light. In addition to the scattered light, the extinction of the light beam may also be measured.

The important advantage of the method according to the invention over the state of the art is that it can identify very small particles and can determine the geometric shape of the detected particles.

The method of identifying particles contained in a gaseous or liquid medium according to the invention may be accomplished with different devices through the application of scattered light measurement. Irrespective of the concrete construction, relatively little space is required by the devices. Therefore, the method can be applied under different environmental conditions using particle measuring equipment that has dimensions and handling properties that permit mobile application of the devices.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawing, wherein similar reference characters denote similar elements throughout the several views.

DETAILED DESCRIPTION OF THE PREFERRED EMBODIMENT

Figure 1:
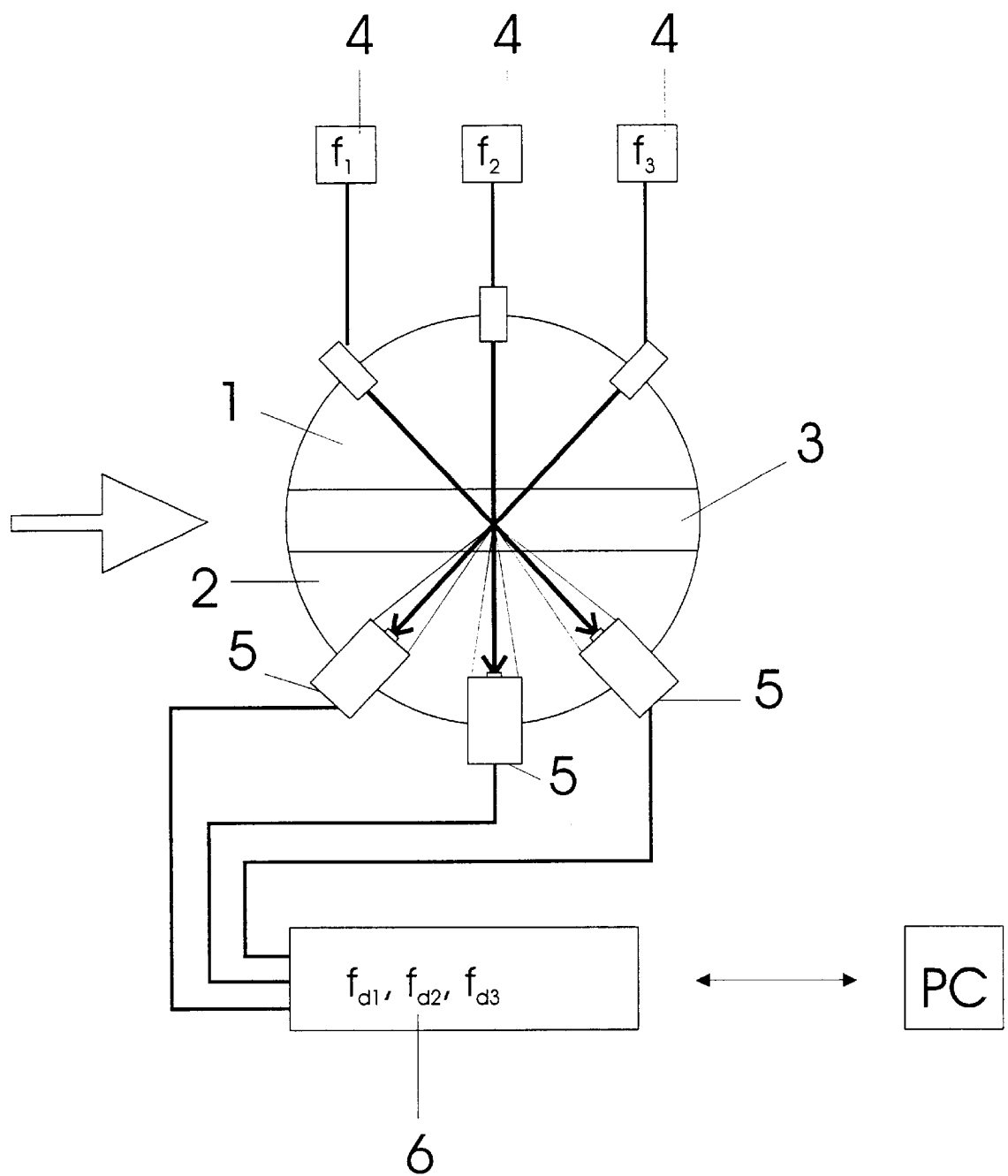
FIG. 1 shows a schematic structure of a device for application of the method according to the invention.
Figure 2:
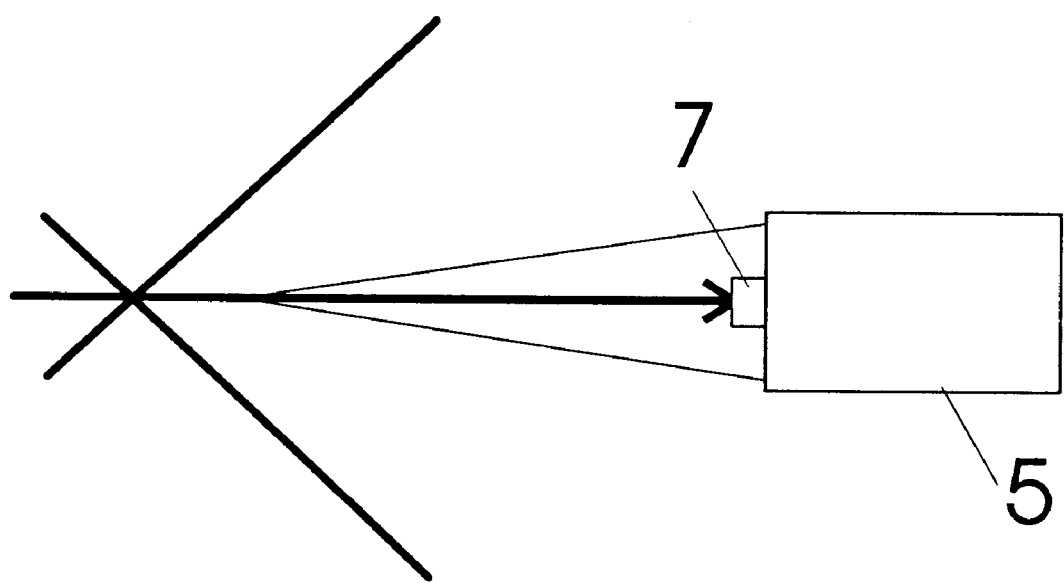
FIG. 2 shows an enlarged view of a section from FIG. 1 in the area of the measuring volume, as well as a detector.

Referring now in detail to the drawings and, in particular, FIG. 1, there is shown two semispherical receiving devices 1 and 2, having an intermediate space 3 between devices 1 and 2. Three light sources 4 are mounted on the top receiving device 1. Laser diodes are preferably used as the light sources 4. Three detectors 5 are arranged on the bottom receiving device 2. Light traps 7 are associated with each detector 5, as shown in FIG. 2. Detectors 5 are connected to an evaluation unit 6 which has a computer if required.

When the method as defined by the invention is applied, the gaseous or liquid carrier medium to be analyzed is passed or guided through intermediate space 3 by suitable aerodynamic or hydrodynamic methods. The carrier medium is symbolized in the drawing by an arrow. The three light sources 4 are activated according to modulation functions $f_1$, $f_2$ and $f_3$, which denote all different kinds of modulation like frequency and modulation amplitude to identify the particles contained in the carrier medium. The light beams of the light sources 4 are aimed at a common measuring volume. The respective laser beams are shown in the drawing. The intersection of the laser beams and the carrier medium must be located in intermediate space 3. This intersection represents the volume of carrier medium to be measured.

The three detectors 5 are operated simultaneously with the three light sources 4. The measured scattered light values acquired by detectors 5 are evaluated and correlated via demodulation functions $f_{d1}$, $f_{d2}$ and $f_{d3}$ in evaluation unit 6 or by a computer. Detectors 5 are operated in such a way that each detector is associated with only one light source. At least two detectors may be evaluated with respect to one common light source, for instance, by using lock-in amplifier technology (or other methods to perform modulation selective measurements) where the signals of the detectors are evaluated according to the modulation of the common light source. Alternatively, each detector may be evaluated with respect to at least two light sources where, as an example, the two light sources are modulated in the same way that the detector, (which is enabled to measure modulation selectively) evaluates the signals from two light sources or the detector evaluates the signals of the two detectors by measuring according to the used modulation of the sources. In any case, the detectors 5 can be selectively evaluated according to frequency with the use of modulated light, which means the different light sources enable the user to measure, evaluate and calculate the light source and detector selectively. The selective measurements enable the user to calculate size, size distribution, shape and material dependent properties of the particles. Furthermore, it is possible to measure the extinction of the incident light in addition to the scattered light by an additional measurement of the light intensity of the not scattered light with the detectors, and calculating the extinction.

Light sources 4 are modulated with signals of different frequencies and/or different phase relations and/or different modulation depths, and the detectors are evaluated according to the kind of modulation by using, for example, lock-in amplifier technology. At least two light sources are modulated with the same signals. Furthermore, it is possible to operate at least one light source with defined polarization of the light by using a light source with a given polarization and a detector system or evaluation unit that is suitable for determining polarization or which is polarization selective, such as polarization filters.

By employing a plurality of light sources that are spaced around the measuring volume, the carrier medium and particles contained therein are illuminated from different angles. It is therefore possible to accurately determine the deviation of the shape of the particle from the ideal spherical form, because another cross section of scatter with the particle is obtained for the various light beams emanating from the several sources by using a light source with a given polarization and a detector system or evaluation unit that is suitable for determining polarization or which is polarization selective, such as polarization filters. Mathematical calculations like scattering theory or comparisons with reference data thus permit conclusions to be drawn with respect to the shape and type of particles present.

Furthermore, the arrangement of the light sources also permits elimination of marginal effects through calculations. These effects are caused if a particle is only partially illuminated by a light source or only partially contained in the measured volume. This also applies to the suppression of coincidences caused by a number of particles that are simultaneously exposed to illumination. The volume measured is limited without requiring shutters or similar optical auxiliary means by the intersection of the various light beams focused on the measured volume, i.e., the measured volume is defined by the beams intersecting one another. Of course, irradiating the volume being measured with a plurality of light sources increases the intensity of the light beamed in, so that smaller particles can also be detected.

By modulating the incident light, it is possible to distinctly enhance the signal-to-noise (S/N) ratio by employing lock-in technology. The use of different frequencies permits exact association of the produced signal with the source by measuring the scattered light. Furthermore, by employing lock-in amplifier technology, it is possible to take into account very weak signals of light scatter. Therefore, the method according to the invention makes it possible to classify particles having a very small particle size within the Rayleigh scattering range.

Simultaneous application of a plurality of light detectors is advantageous as well. Like the light sources, the detectors are arranged spaced around the volume being measured. The readout of the detectors and the measurement of the scattered light is frequency-selective. This way, the advantages of lock-in amplifier technology can be employed and the scattered light signals can be clearly associated with the sources of the light. This means that each of the detectors arranged around the volume being measured picks up the scattered light of each source. According to the method of the invention, the scattered light of one source is simultaneously detected with angle resolution by all detectors, and the signals of all light sources arranged at different angles are selectively detected by one detector in the same measuring process.

Measuring the scattered light under different angles in different planes of scatter is required in order to obtain correct statements on the shape of the particles, because the scattered light is highly dependent upon the orientation of the particle relative to the incident light beam, especially in connection with nonspherical particles.

Acquisition of all the data described above is carried out in one step on each particle by employing modulation frequencies tuned to the particle speed. The correlated evaluation of all measured data obtained therefore permits determination of the concentration, size, size distribution and shape of the particles contained in the carrier medium to be analyzed.

Accordingly, while only a few embodiments of the present invention have been shown and described, it is obvious that many changes and modifications may be made thereunto without departing from the spirit and scope of the invention.

What is claimed is:

1. A method for identifying the size, shape and material properties of particles contained in a liquid or gaseous carrier medium using scattered light measurement, comprising:

aiming at least three physically different light sources not originating from a common light source simultaneously at a common volume of carrier medium to be measured;

operating at least three detectors simultaneous with the light sources, said detectors detecting scattered light from said light sources; and correlating and evaluating said detected scattered light using signals from the detectors to identify the size, shape and material properties of the particles.

2. The method according to claim 1, wherein each light from only one light source is evaluated with respect to each detector.

3. The method according to claim 1, wherein light from a common light source is evaluated from signals from at least two detectors using lock-in amplifier technology.

4. The method according to claim 1, wherein light from at least two light sources is evaluated from signals from each detector by measuring according to the used modulation of the light sources.

5. The method according to claim 1, wherein the light sources are modulated with signals having different frequencies using lock-in amplifier technology.

6. The method according to claim 1, wherein the light sources are modulated with signals having different phase relations using lock-in amplifier technology.

7. The method according to claim 1, wherein the light sources are modulated with signals having different modulation depths using lock-in amplifier technology.

8. The method according to claim 1, wherein at least two light sources are modulated with the same signals.

9. The method according to claim 1, wherein at least one light source is operated with a defined polarization by using a light source with a given polarization and a detector system that is adapted to determine polarization.

10. The method according to claim 1, wherein the step of evaluating is frequency-selective through the use of modulated light.

11. The method according to claim 1, wherein extinction of the light is also measured by measuring the light intensity of the not scattered light with said detectors and calculating the extinction.

* * * * *